US009752183B2

(12) United States Patent
Hoffmann et al.

(10) Patent No.: US 9,752,183 B2
(45) Date of Patent: Sep. 5, 2017

(54) MULTIPLEXED DIGITAL PCR

(71) Applicant: Albert-Ludwigs-Universitaet Freiburg, Freiburg (DE)

(72) Inventors: Jochen Hoffmann, Freiburg (DE); Guenter Roth, Freiburg (DE)

(73) Assignee: ALBERT-LUDWIGS-UNIVERSITAET FREIBURG (DE)

( * ) Notice: Subject to any disclaimer, the term of this patent is extended or adjusted under 35 U.S.C. 154(b) by 36 days.

(21) Appl. No.: 14/375,817

(22) PCT Filed: Feb. 1, 2013

(86) PCT No.: PCT/EP2013/052063
§ 371 (c)(1),
(2) Date: Jul. 31, 2014

(87) PCT Pub. No.: WO2013/113889
PCT Pub. Date: Aug. 8, 2013

(65) Prior Publication Data

US 2014/0378320 A1 Dec. 25, 2014

(30) Foreign Application Priority Data

Feb. 1, 2012 (DE) ........................ 10 2012 100 824

(51) Int. Cl.
*C12Q 1/68* (2006.01)

(52) U.S. Cl.
CPC ........... *C12Q 1/686* (2013.01); *C12Q 1/6837* (2013.01); *C12Q 1/6876* (2013.01); *C12Q 2600/16* (2013.01)

(58) Field of Classification Search
None
See application file for complete search history.

(56) References Cited

U.S. PATENT DOCUMENTS

| | | | | |
|---|---|---|---|---|
| 2005/0220675 | A1 | 10/2005 | Reed et al. | |
| 2012/0264132 | A1* | 10/2012 | Ismagilov | C12Q 1/6851 435/6.12 |
| 2012/0329038 | A1* | 12/2012 | Ismagilov | C12Q 1/6851 435/5 |
| 2013/0280725 | A1* | 10/2013 | Ismagilov | B01L 3/5027 435/6.12 |
| 2013/0281316 | A1* | 10/2013 | Ismagilov | C12Q 1/686 506/9 |
| 2013/0296194 | A1* | 11/2013 | Jacobson | C12N 15/10 506/16 |
| 2013/0309679 | A1* | 11/2013 | Ismagilov | C12N 15/1003 435/6.12 |
| 2014/0287423 | A1* | 9/2014 | Nurse | B01L 3/502707 435/6.12 |

FOREIGN PATENT DOCUMENTS

| | | | | |
|---|---|---|---|---|
| WO | 2010/019388 | A2 | 2/2010 | |
| WO | 2010/077618 | A1 | 7/2010 | |
| WO | WO 2010111265 | A1 * | 9/2010 | B01L 3/502738 |
| WO | WO 2013138767 | A1 * | 9/2013 | B01L 3/50857 |

OTHER PUBLICATIONS

Shen et al. (Digital PCR on a SlipChip, Lab Chip. Oct. 21, 2010; 10(20): 2666-2672, Published online Jul. 1, 2010.*
Du et al. (SlipChip, Lab Chip. Aug. 21, 2009; 9(16): 2286-2292, Published online May 15, 2009).*
Stedtfeld et al. (Development and Experimental Validation of a Predictive Threshold Cycle Equation for Quantification of Virulence and Marker Genes by High-Throughput Nanoliter-Volume. PCR on the OpenArray Platform, Appl Environ Microbiol. Jun. 2008;74(12):3831-8. Epub Apr. 18, 2008).*
Qi Zongtai et al: "Digital analysis of the expression levels of multiple colorectal cancer-related genes by multiplexed digital-PCR coupled with hydrogel bead-array.", in: The Analyst, vol. 136, No. 11, Jun. 7, 2011, pp. 2252-2259.
Bhat Somanath et al: "Single molecule detection in nanofluidic digital array enables accurate measurement of DNA copy number", in: Analytical and Bioanalytical Chemistry, Springer, Berlin, DE, vol. 394, No. 2, May 1, 2009, pp. 457-467.
Cohen Dawn E et al: "Self-digitization of sample volumes.", in: Analytical Chemistry Jul. 1, 2010, vol. 82, No. 13, Jul. 1, 2010, pp. 5707-5717.
Wang Jun et al: "A novel nanofluidic digital-PCR platform to study MET receptor genomic amplification and mutation in lung cancer", in: American Association for Cancer Research. Proceedings of the Annual Meeting, American Association for Cancer Research, US, vol. 50, Apr. 1, 2009, p. 1254.
Bhat et al., Single Molecule Detection in Nanofluidic Digital Array Enables Accurate Measurement of DNA Copy Number, Anal. Bioanal. Chem., vol. 394, 2009, pp. 457-467.
Cohen et al., Self-Digitization of Sample Volumes, Anal. Chem., vol. 82, 2010, 5707-5717.
Qi et al., Digital Analysis of the Expression Levels of Multiple Colorectal Cancer-related Genes by Multiplexed Digital-PCR Coupled with Hydrogel Bead-array, Analyst, vol. 136, 2011, pp. 2252-2259.
Wang et al., A Novel Nanofluidic Digital-PCR Platform to Study MET Receptor Genomic Amplification and Mutation in Lung Cancer, abstract 5199, 100th AACR Annual Meeting, Apr. 2009, pp. 1-2.

* cited by examiner

*Primary Examiner* — Aaron Priest
(74) *Attorney, Agent, or Firm* — Agris & Von Natzmer, LLP; Joyce v. Natzmer

(57) ABSTRACT

The invention relates to a method for detecting at least one target molecule and/or product molecule, wherein reaction components are provided in defined regions of a base surface and/or covering device. At least two defined regions with different reaction components are provided, and an amplification reaction is carried out. The invention also relates to a device for carrying out said method.

23 Claims, 3 Drawing Sheets

1.1

1.2

A

B

4/4

MULTIPLEXED DIGITAL PCR

CROSS-REFERENCE TO RELATED APPLICATIONS

Figure 1:
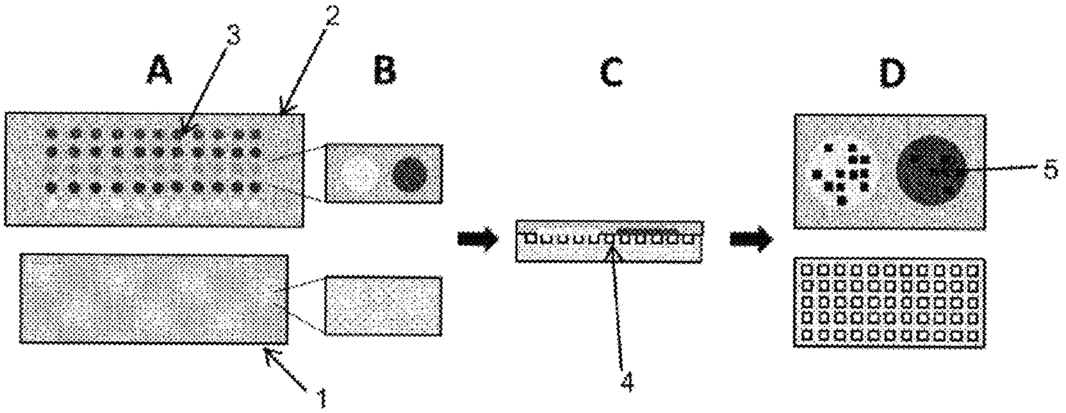
Figure 1:
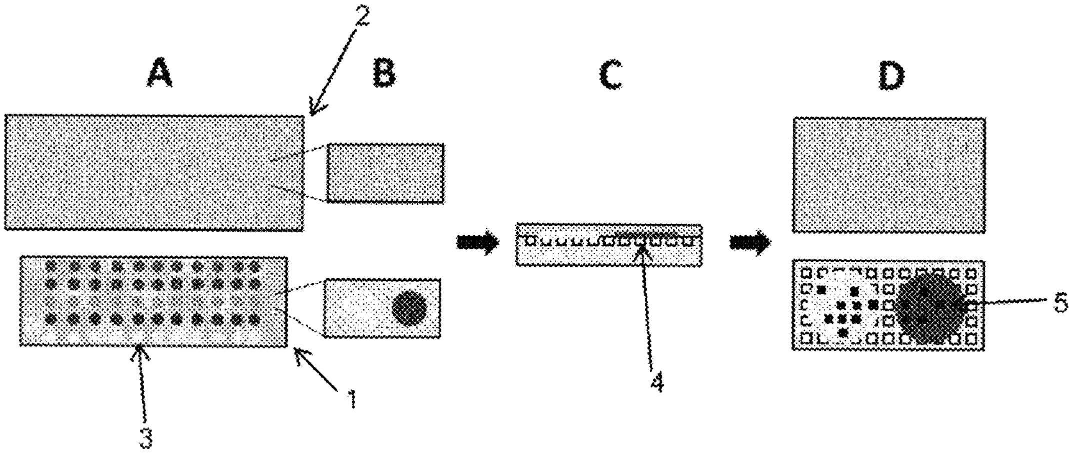

This is the U.S. national stage of International application PCT/EP2013/052063, filed Feb. 1, 2013 designating the United States and claiming priority to German application DE 10 2012 100 824.8, filed Feb. 1, 2012.

The invention relates to a method for detection of at least one target molecule and/or product molecule, wherein reaction components are made available in defined regions of a base surface and/or covering device, wherein there are at least two defined regions with different reaction components, and wherein an amplification reaction is carried out. The invention furthermore relates to an apparatus for carrying out the said method.

STATE OF THE ART

In the prior art, numerous investigation methods of molecular biology are described, which allow detection and, if applicable, analysis of a biological sample. One of these methods is detection and parallel analysis of several thousand individual detections in a small amount of biological sample material by means of a microarray. There are different forms of microarrays, which are sometimes also referred to as "gene chips" or "biochips," because, like a computer chip, they can contain a lot of data in a very small space.

Microarrays allow highly parallel detection of different target molecules on a typically planar substrate. The immobilized probe molecules of a microarray are immobilized or synthesized on a suitable substrate, during the course of the production process, at a defined location (spot) of a grid (array), by means of transfer of small volumes of liquid. This two-dimensional immobilization of capture molecules, with local resolution, can be structured in such a manner that nucleic acids or peptides, i.e. proteins, can be detected. In general, in situ lithography methods only allow synthesis of short oligonucleotides or amino acid chains. The DNA microarrays produced, however, can be stored for months under suitable conditions, but protein arrays can be stored functionally only for a short time.

For a DNA microarray analysis, the sample to be investigated is mixed with a suitable buffer and incubated with the microarray in an appropriate manner, so that typically, in the case of complementary sequence sections, a hybridization event takes place. Because of the low sensitivity of microarray systems, if nucleic acid is to be detected, the sample is amplified in a prior reaction step (e.g. by means of Polymerase Chain Reaction (PCR), RT-PCR or Whole Genome Amplification (WGA)), and marked with a fluorescent marker for detection, for example, or incubated with an additional detection probe on the microarray. Peptides and proteins cannot be amplified enzymatically, and are concentrated by means of purification of the sample to be investigated. In contrast to this there are approaches that carry out signal amplification on the microarray after hybridization has taken place, for example by means of Rolling Circle Amplification (RCA). This method of procedure comprises multiple time-intensive work steps and increases the risk of inaccuracies and contaminations. Microarrays are typically used in expression analyses and in the detection of pathogens or resistance markers. An overview of various production techniques and uses is known to a person skilled in the art from the prior art.

Microarray analyses comprise multiple work steps, namely typically selection of the sequence of an immobilized capture molecule, sample preparation and amplification, hybridization or incubation, followed by subsequent washing steps as well as signal measurement and data processing. The microarrays described in the prior art until now are based on the principle of direct interaction between the target molecule and the immobilized capture molecule, and for this reason, a modified capture molecule must be used as soon as a deviating target molecule is to be detected. This fundamentally requires the production of a modified array, and is a significant time and cost factor. Because of the complicated production process, larger numbers of a sequence layout are produced for economic reasons. Therefore working with microarrays offers little flexibility with regard to the target molecule to be detected, because a modified sequence layout brings with it high consequential costs and immense processing effort.

Furthermore, universal microarrays are disclosed in the prior art. Universal nucleic acid microarrays, in which the sequence of the immobilized capture molecules is independent of the target sequence, are commercially available, for example Affymetrix "GeneChip Universal Tag Arrays." These methods are based on a universal microarray sequence layout in which the immobilized oligonucleotides (ZIP code or Universal Tag) are independent of the sequence to be detected and do not interfere with this sequence. In a typical detection reaction, the target sequence is generally amplified in a separate reaction vessel and purified, if necessary. Subsequently, a ligation step takes place, in which a specific detection probe and a fluorescence probe hybridize directly next to one another, in the presence of the target sequence, on the base sequence of the target sequence. The detection probe possesses an overhang not specific to a target sequence (complementary ZIP code, cZIP code), which serves as an addressing sequence and is complementary to a ZIP code probe of the microarray. As a result of the ligation, a product of detection probe and fluorescence probe occurs, which is used for hybridization on a ZIP code microarray. A fluorescence signal at a specific ZIP code spot is an indirect indication of the presence of the target sequence in the reaction mix. Coded microbeads (beads) can also be used as the solid phase. In this connection, a clearly identifiable bead is assigned to each capture molecule, and this is achieved by means of a defined nucleotide sequence, or by means of coloration or intensity. In a later work step, automatic detection of the bead as well as the parallel analysis can be carried out as a result of this assignment. This method possesses the advantage that the beads are present in homogenized form in the liquid phase, and the resulting reaction kinetics are higher than in the case of comparable liquid phase/solid phase interactions.

Furthermore, PCR is described in the prior art. PCR is a preferably temperature-controlled enzymatic reaction that can produce an amplificate of DNA that is present (sample fragment). The amplification takes place essentially using enzymes, energy, and dNTPs (deoxyribonucleoside triphosphates). dNTPs are molecular monomers, namely dATP (deoxyadenosine triphosphate), dGTP (deoxyguanosine triphosphate), dTTP (deoxythymidine triphosphate), dCTP (deoxycytidine triphosphate), which are needed for the synthesis of a DNA strand during amplification. If RNA is present as a sample fragment for amplification, an RNA polymerase is used instead of DNA polymerase, and dUTP (deoxyuridine triphosphate) is used instead of dTTP.

A form of PCR is digital PCR (dPCR). A possibility for achieving digitality is diluting the sample in such a manner that either no (=0) or one (=1) DNA molecule is present in a reaction volume (or reactor or microreactor), and thus a great number of PCR reactions can be carried out. By means of enzymatic PCR amplification and quantification of the amplificates, it is possible to determine whether the reaction volume is negative (=0) or positive (=1). In a reaction space, an amplificate is generated only if at least a single DNA molecule was present in the reaction space. By means of counting out the positive signals, the sample to be amplified can be quantified. Furthermore, the amplificate can also be bound to a solid phase (e.g. by way of a primer extension reaction) if the dPCR is connected with a solid-phase PCR.

In the literature, fundamentally two different systems are described for carrying out digital PCR: The first system comprises what is called oil/emulsion PCR (emPCR), which represents a droplet-based system. In this connection, millions of droplets that contain individual DNA molecules form PCR reaction spaces, with the droplets being generated microfluidically in an oil matrix. After the PCR reaction, the target molecules can be determined by means of quantification of the positive signals in the droplets. In order to use an emPCR batch for detection of more than one genome segment, in other words to make emPCR capable of multiplexing, the amplified DNA is either sequenced, which is expensive and time-consuming, or the sequences are differentiated using a mix of Taqman probes. However, this method is currently limited to fewer than five target molecules. Although the oil-based amplification methods achieve a great number of possible reactions, the emPCR systems suffer from the fact that they have only insufficient amplification efficiency and are complicated to carry out. For example, numerous and, above all, time-consuming method steps as well as expensive equipment are required. A further intrinsic disadvantage of emPCR is that the production of the droplets is very time-consuming, and the droplets can merge, and this in turn can lead to false results.

The second system in the prior art for carrying out digital PCR comprises what are called PCR microreactors, which are implemented on a chip and are characterized by a closed architecture. The microreactors are sealed either mechanically or by means of a second liquid phase (e.g. oil). In contrast to this, open systems use microreactors that are closed off by means of a membrane, silicone layers, mineral oil or by means of a SlipChip system. A significant disadvantage of on-chip digital PCR systems is that only one target sequence per chip and sample can be analyzed in the systems.

It is a further disadvantage of the systems disclosed in the prior art that these allow little possibility for multiplexing, because of their structures, and furthermore are dependent on special laboratory equipment. Another disadvantage is that in the prior art special devices are generally required for processing. A main disadvantage is that detection of only a few target sequences ("targets") is possible. Depending on the system, the number of detectable target sequences is restricted to one or maximally 144 targets (Applied Bioscience).

Furthermore, the systems in the prior art are inflexible and complex in the sense that modification of the system for different target sequences involves greater effort. At present, it is still necessary to quantify a sample solution ahead of digital PCR in order to obtain results that can be evaluated.

In most systems from the prior art, the reactors or reactor spaces have a uniform size, for which reason the concentration first has to be determined, in order to arrive precisely at the reaction regime of less than one DNA sequence per cavity. An overly high concentration of DNA generates only positive cavities and thereby saturation; an overly low concentration of DNA yields only few individual signals and thereby very poor statistics.

In the prior art, a method and apparatus for the detection of DNA molecules using a sensor array are furthermore disclosed in U.S. Pat. No. 6,482,593. This array is a structured multi-well array that has immobilized biosensors at discrete locations. However, no amplification reaction takes place.

For real-time detection of the reaction, ever more complex and expensive equipment is required, and this is an additional disadvantage. The components of current systems are complex, in part, and therefore expensive to produce. Often, no disposable articles are available.

The systems in the prior art that use oil for the production of individual reaction compartments demonstrate the disadvantage of the instability of the reaction compartments produced in this way, because individual droplets can merge with one another during the reaction and therefore the informational value of the entire reaction is lost. In order to be able to identify multiple target sequences, sequencing takes place in many systems from the prior art. This in turn is expensive and very time-consuming. Furthermore, many systems demonstrate poor reaction efficiency or require complicated reaction management.

Accordingly, it was the task of the present invention to make available a method and an apparatus that do not demonstrate the disadvantages or deficiencies of the prior art.

DESCRIPTION OF THE INVENTION

This task is accomplished by means of the independent claims. Advantageous embodiments are evident from the dependent claims.

The invention relates, in a first preferred embodiment, to a method for detection of at least one target molecule and/or product molecule, comprising the following steps:

a) making available an apparatus, wherein
  (i) the apparatus comprises a base surface with cavities and
  (ii) a covering device, and wherein
  (iii) reaction components are made available on the base surface and/or the covering device, in defined regions, wherein there are at least two defined regions with different reaction components,
b) arranging the base surface and covering device relative to one another,
c) adding a reaction solution to the base surface, wherein the reaction solution penetrates into the cavities, and wherein the reaction solution contains the target molecules,
d) carrying out an amplification reaction, a detection reaction and/or a derivatization reaction, wherein the reaction solution comes into contact with the reaction components and product molecules are formed, and
e) detecting at least one target molecule and/or product molecule, wherein at least two different sections of the target molecule and/or product molecule are detected in separate, defined regions and/or at least two different target molecules and/or product molecules are detected in separate, defined regions.

As soon as the covering device and the base surface are arranged relative to one another, they form a plurality of reaction spaces. The reaction spaces are preferably formed in part by the cavities. In this connection, it is preferred that the reaction spaces are separated from one another and therefore no mixing can take place. It is preferred that the resulting reaction spaces are closed off and that each cavity forms a reaction space.

It is particularly preferred that the covering device is a microarray and the defined regions are spots of the microarray. A microarray in the sense of the invention is preferably characterized by the regular placement of spots on a substrate material. It is preferred that the spots have a diameter of 0.1 $\mu m^2$-10 $cm^2$. The geometry of the spots can preferably be square, rectangular, round, oval, triangular, hexagonal, octagonal or polygonal. However, any other shape not explicitly mentioned here can be desirable and advantageous under certain conditions. It is also possible that the spots represent notches in the covering device, wherein the spots can differ in terms of their depth or other characteristics. Furthermore, the spots can be disposed in different arrangements relative to one another, regularly or irregularly. If a microarray is used as the covering device, it is preferred that the reaction components are made available in the microarray, particularly preferably in the spots of the microarray, very particularly preferably supplied there.

However, the invention also relates to the method, wherein the reaction components are made available, preferably supplied in the cavities of the base surface. In such a case, a simple substrate can be used as the covering device instead of a microarray.

In this connection, the reaction components can possess different constituents and functions, thereby making it possible to analyze different regions of a target molecule, for example, by means of PCR, in one apparatus (base surface or covering device). Accordingly, different reactions can be carried out on one apparatus, and this significantly reduces the work effort and the costs, and furthermore provides a practical tool for diagnosis, for example.

It is furthermore preferred that the defined regions lie in the cavities of the base surface. The geometry of the cavities of the base surface can preferably be square, rectangular, round, oval, triangular, hexagonal, octagonal or polygonal. However, any other shape not explicitly mentioned here can be desirable and advantageous under certain conditions. It is also possible that the cavities differ in terms of their depth or other characteristics. The cavities can furthermore be disposed in different arrangements relative to one another, regularly or irregularly. The base surface in the sense of the invention can also be referred to as a chip, and the cavities can also be referred to as reactors. The cavities in the sense of the invention are preferably individual compartments. Thus, a separate detection reaction, for example PCR, can take place in every cavity, if a target molecule is present.

It is furthermore preferred that the base surface has 1 to 10ˆ10, preferably 10ˆ2 to 100̂ 8, particularly preferably 10ˆ4 to 10ˆ6 cavities and/or that the cavities possess a volume of 1 fL to 1 mL.

It is furthermore preferred that the base surface has a liquid barrier that forms an edge around the cavities of the base surface. The liquid barrier particularly refers, in the sense of the invention, to a barrier for the reaction solution that has been introduced, so that this solution does not exit beyond the edge of the base surface. The barrier can advantageously be a physical and/or chemical barrier. In this connection, this can preferably be a hydrophobic region or a frame that runs around the base surface and thereby represents a delimitation with regard to the surroundings. The covering device can be laid onto or into the inner region of the barrier, in order to produce closed-off reaction spaces within the apparatus. This means that the covering device preferably lies on at least part of the cavities. The barrier serves to ensure that the reaction solution gets exclusively into the cavities. In the sense of the invention, the barrier can particularly also be referred to as a guide rail for liquids, because the reaction solution can penetrate into the regions intended for it, in this way.

It is preferred that after the cavities are filled and closed off with the covering device, the barrier encloses the covering device and the latter is therefore surrounded by a raised frame. By means of this embodiment, a particularly well-sealed apparatus is made available. It is furthermore preferred that each cavity forms a closed reaction space with the covering device.

It is preferred that the reaction components are present on the covering device and/or the base surface over the full area or in certain regions. In the case of availability in certain regions, one, two or more different reaction components are supplied per spot or per cavity.

The reaction components preferably comprise primers, probes, intercalating pigments, polymerases, further enzymes and/or reaction-improving components. In this connection, it is particularly preferred that the reaction components are supplied in the cavities of the base surface and/or the spots of the covering device. These reaction components can be introduced into spatially delimited regions of the base surface and/or of the covering device, using a spotting method (e.g. TopSpot system).

Reaction-improving components preferably comprise "bovine serum albumin" (BSA), agarose, Tween, ultrasounded nucleic acids and/or a UNG digestion system.

The length of the primers usually lies between 1 and 10ˆ3 individual molecules. Primers in the sense of the invention preferably contain a binding location for target molecules, preferably DNA molecules. The primers can contain a chemical coupling group at one or more ends, for oriented binding to a surface. This group can be, among other things, biotin, double biotin, NH2, SH, acrydite or a polynucleotide sequence. Furthermore, the primers can be usual tags or binders such as streptavidin, His tag, nickel NTA, myc or flag tag, or the like. The primers can additionally contain marking sequences, aside from the detection-specific sequence. These marking sequences can be not only DNA, fluorophores, but also other molecules.

The primers can be liquid-phase primers or solid-phase primers. If they are solid-phase primers, they can be immobilized either directly or indirectly. Methods for direct immobilization of nucleic acids can preferably be: hydrogels, UV crosslinking, copolymerization in acrylamide gels, affinity binding (avidin-streptavidin), ionic or absorptive binding. Methods for indirect immobilization use linker molecules, for example homo-bifunctional or hetero-bifunctional linker molecules. The homo-bifunctional linker can be PCITC, for example. In general, the resulting binding of the primers to a solid phase is compatible with amplification reactions and the derivatization that might follow.

Furthermore, a spacer molecule can be present between the coupling group and the nucleic acid sequence. The spacer can consist, among other things, of a carbon chain or a polynucleotide sequence (poly-T sequence).

The primers can furthermore contain promoter locations and/or binding locations for an RNA polymerase or a cell-free expression system.

Furthermore, only one of the primers can be bound to the surface, and the other can be present in soluble form (usual solid-phase PCR), or both primers can be bound to the surface (corresponds to bridge amplification). These methods differ from the prior art, however, in that they are spatially limited. Bridge amplification can only take place in the interior region of a cavity and cannot leave the cavity because of the spatial separation, although the complete surface around the cavity might also permit bridge amplification.

Preferably, the reaction components or parts of them are immobilized on the base surface and/or the covering surface. It is particularly preferred that reaction components or parts of them are covalently bound to the surface and/or the covering device. If primers are immobilized on the base surface and/or the covering device, it is additionally made possible to carry out bridge amplification. This reaction then takes place exclusively by way of solid-phase primers, and preferably no liquid-phase primers are present in the system.

The method can therefore also preferably be solid-phase PCR (also called SP-PCR). This is a PCR reaction in which one of the two primers is immobilized on a solid phase (e.g. the covering device). The PCR product generated within the scope of PCR is bound to the solid phase by way of this solid-phase primer.

The base surface in the sense of the invention can also be referred to as a reactor chip. Such a reactor chip is preferably a "convenient product," which is preferably offered for sale as a disposable article.

It is furthermore preferred that a spot of the covering device covers multiple cavities of the base surface after the covering device and the base surface are arranged relative to one another. Therefore the product molecules and/or target molecules of multiple cavities can be analyzed on one spot.

It is particularly preferred that the method is a digital method. In the sense of the invention, digitality preferably means that one or no target molecule comes onto a defined region, on average. However, digitality in the sense of the invention also means that if different target molecules are detected, only one type of target molecule is present in a defined region, on average, so that there are more defined regions than target molecules per type of target molecule. Digitality in the sense of the invention furthermore preferably also means that if multiple sections of a target molecule are supposed to be detected, only one section of a target molecule is detected in a defined region, on average. In this case, the number of target molecules is therefore not necessarily lower than the number of defined regions, but the reaction components supplied lead to digitality, because the same reaction components are not supplied in each defined region.

In this connection, the method of functioning of the digital method can be influenced, among other things, by way of the geometry of the cavities and/or spots or also by way of the number of cavities and/or spots.

The invention combines the technology of DNA microarrays with digital reactions, preferably digital PCR reactions, in order to thereby be able to carry out digital PCR on every spot of the covering device or in every cavity of the base surface. This allows the detection of more than one target molecule or multiple sections of a target molecule. By means of this multiplexing, corresponding to a microarray while maintaining the advantages of digital PCR, the method can be used, in the sense of the invention, particularly preferably in diagnostics. Multiplexing, in the sense of the invention, particularly refers to the analysis of numerous individual reactions to produce a result. It is particularly preferred that the amplification step is digital PCR and/or digital solid-phase PCR.

It is particularly preferred that the method is used to carry out digital PCR (dPCR). In this connection, the base surface is filled with a sample, which can also be contained in a reaction solution, in the sense of the invention, and closed off with the covering device. Subsequently, digital PCR is carried out. After use, the base surface can be disposed of.

Digital PCR in the sense of the invention means reactions in which digitality can be achieved in different ways. For one thing, it is possible that the number of defined regions (cavities or spots) is greater than the number of target molecules that are distributed over the defined regions. If different target molecules are detected, digitality can also be achieved in that the number of defined regions (cavities or spots) is greater than the number of a respective type of the target molecule. However, it is also preferred that the reaction components are supplied and that a type of primers (for example for a specific target molecule or a specific segment of a target molecule) is present, in each instance, in a lower number than there are defined regions (cavities or spots), for example.

It was completely surprising that such an omnipotent and flexible detection system can be created by means of the combination of established DNA microarrays with a base surface that contains cavities for digital PCR. Viewed technically, the unique possibilities of digital PCR are preferentially connected with the multiplexing properties of microarrays. By means of the said combination, this system is given outstanding characteristics that far exceed those of systems known from the prior art.

It was very surprising that even reaction solutions with a high concentration of target molecules do not represent any limitation for the apparatus and the method of the invention, and that digital PCR can also be carried out. Even in the event that the target molecules, preferably DNA target molecules, are present in greatly diluted form, digital PCR can surprisingly be carried out, in that a large volume is analyzed. By means of a statistical method (particularly the MPN/Most Probable Number method), it is furthermore possible to extract data that can be evaluated from an apparatus having a large volume. This method is preferably used when the result does comprise 0 and 1 but also "more" DNA. For this purpose, the method determines the positive results of a dilution series and calculates the most probable number of the initial DNA concentration per volume from them. In this way, the statistical validity can be extremely improved. In a preferred embodiment, the digital method is a subgroup of the MPN method. Because the volumes of the cavities can easily be adapted to the amount of DNA in a sample to be analyzed, analysis of any imaginable DNA sample or concentration is possible. Therefore a significant disadvantage of the methods described in the prior art can be eliminated, namely that every PCR method is limited by the DNA concentration. This disadvantage can preferably be circumvented by means of the dilution steps in the cavities.

It can also be preferred that the reaction components are supplied in the cavities of the base surface, so that the base surface represents a microarray. In this case, it is also possible that reaction components (e.g. primers and/or probes) were applied to the covering device, over its full area.

The invention therefore preferably represents a combination invention. This is because preferably the known elements of PCR and of a microarray are combined with one another. The surprising effects that result from this are, for example, the precision of the methods being carried out, and the high degree of multiplexing, which is made possible for the first time, by means of the invention, in simple and cost-advantageous manner.

The detection of the target molecules in the sense of the invention can take place in different ways. A person skilled in the art knows different methods for detecting amplificates of a PCR reaction, for example. For one thing, the reaction can take place on the surface of the covering device or of the base surface. However, it is also possible that the reaction takes place in the volume that is formed by the enclosed region between the covering device and the base surface. However, a combination of all three mechanisms with one another is also possible.

For detection on the surface of the covering device or the base surface, surface-bound PCR products can be detected with intercalating pigments, for example. It is also possible to carry out the detection by way of coupling of streptavidin-conjugated fluorophores or a hybridization reaction. Furthermore, in digital PCR, a signal can be generated on a surface. This can be done, for example, by means of RCA (Rolling Circle Amplification), hybridization of a fluorescent PCR product on complementary solid-phase primers, or a special detection assay. All these methods can take place as an end point measurement after the amplification reaction. However, a real-time measurement can already take place during the reaction, by means of surface-sensitive methods, e.g. confocal laser microscopy, ATR measurements, Biacore, etc. This has the advantage, for certain reactions, that the reaction can still be influenced. A person skilled in the art knows in what manner detection of reaction products can be carried out, and is able to select a suitable method depending on the target molecule or product molecule, without having to perform any inventive activity in this connection.

For example, detection can take place directly after the amplification reaction, without any specific detection reaction, by means of intercalating pigments (for example Sybr Green or ethidium bromide), or by means of primers labeled with fluorophores, in the amplification reaction. For this purpose, a washing step and disassembly are then required, so that the base surface and/or the covering device can be washed.

If detection takes place not on a surface, it can take place during the amplification reaction, by means of an intercalating pigment or by means of a suitable probe system, in real time. For this purpose, all the methods of conventional real-time PCR are possible, as are directly intercalating pigments (ethidium bromide, Sybr Green), Taqman or high-probe probes, etc. Thus, the increase in fluorescence can already be measured during the reaction. However, a generated amplificate can also be measured as an end product. The methods mentioned above can also be used here. In both cases, a fluorescence signal can be detected in the respective cavities or the spot.

On the basis of colored multiplexing as it is possible in Taqman PCR, it is also possible here to amplify up to 10 different target molecules or target molecule segments in parallel, within the defined regions. Therefore it is then possible to carry out a digital amplification reaction in different colors, and thereby to increase the occupation density of the system in accordance with the number of colors used. One of the colors can furthermore be used as a reference, which provides information as to whether or not an amplification reaction has taken place and as to how strong the amplification signal is. Therefore internal calibration and, at the same time, a positive control are possible, which makes it possible to recognize even weak signals as such and to evaluate strong signals as artifacts or true measurement values.

The reaction solution contains the target molecules. It is furthermore preferred that the reaction solution comprises nucleic acids, proteins, natural substances, intercalating pigments, enzymes, additives, viruses, prokaryotes, eukaryotes, fragments of synthetic molecules and/or biomolecules.

The reaction solution, together with the reaction components, preferably contains the totality of all the molecules that allow producing amplificates of a target molecule, particularly of a DNA sample fragment. The composition of the reaction solution and of the reaction components clearly establishes what target molecules or what sections of target molecules are amplified in what manner. The reaction solution preferably comprises individual building blocks for the synthesis of the amplificates, an energy system and/or a synthesis system. Preferably, a DNA polymerase, particularly a Pfu or Taq polymerase, is included, along with dNTPs or a mix of dATPs, dCTPs, dGTPs, dTTPs, and dUTPs, and, in particular, a UNG digestion system. Furthermore, reaction-improving components can preferably be present in the reaction solution. These are preferably "bovine serum albumin" (BSA), agarose, Tween, ultrasounded nucleic acids and/or a UNG digestion system. It can also be preferred that the reaction solution contains an RNA polymerase. This can also particularly be a commercially available PCR amplification mix, into which the target molecules are placed.

The target molecules can be poly-nucleic acids, such as DNA, cDNA or RNA molecules, but also proteins, antibodies, synthetic organic molecules or natural substances. If the target molecules are not poly-nucleic acids, these can be amplified and/or derivatized directly or indirectly, by way of a built-in label of DNA or RNA. In the most usual case, the target molecules are DNA. The DNA molecules can be obtained, among other things, from viruses, prokaryotes and/or eukaryotes and/or be of a synthetic nature. The length of a target molecule can be between 1 and 10^10 individual monomers. Such target molecules can also be divided into individual fragments, according to different methods. The fragments can furthermore be single-stranded or double-stranded. In the sense of the invention, the target molecules can also be referred to as samples or targets.

If the target molecule is not DNA or RNA, it is preferred that the target molecule has a built-in label of DNA or RNA. This label can then be detected by way of the method described.

It is preferred that the target molecules have adaptors with a uniform sequence on at least one end. The preferred length of the adaptors lies between 1 to 1000 individual molecules. The adaptors can have different functional units. Adaptors are preferably present at the beginning and the end of a target molecule, in the form of uniform and clear sequences. They define those regions of the target molecule that are being amplified. The adaptors function as a primer, particularly for PCR. Either all or only specific subunits of the totality of all the target molecules can be amplified by means of the adaptors. Furthermore, the adaptors can preferably possess multiple different functional units, one behind the other, which can particularly be binding locations for RNA polymerases or cell-free expression systems. The adaptor sequences can be derived, for example, from common sequencing systems (among others, Applied Biosystems/Life Technologies, Ion Torrent/Life Technology, Roche, Illumina, George Church/Dover Systems), and, in this connection, can be sequence-identical or can contain further sequences or modifications. In this way, the adaptor sequences can create a sequencing-capable surface. The surface is sequencing-capable if amplified target molecules have bound to the capture molecules. The amplificates are then available for further studies.

It is preferred that a sample to be analyzed is diluted, particularly before introduction into the base surface. By means of the introduction of the sample solution into the base surface, the sample is divided up among many cavities, which is also known to a person skilled in the art as "aliquoting."

Product molecules are, in the sense of the invention, preferably those molecules that are formed during the method according to the invention, by means of the amplification and/or derivatization of the target molecules. In this way, the presence of the target molecules can also be detected by way of the detection of the product molecules.

It is preferred that 1 to 10^10 product molecules, preferably amplificates, are generated.

The reaction solution can be introduced into the cavities of the base surface by way of centrifugation, vacuum, atomization, immersion, dip-coating or spreading, among other things. Depending on the number of target molecules introduced into the reaction solution, between 1 and 10^10 target molecules are introduced into the apparatus. Furthermore, it is preferred that each cavity contains between 1 and 10 target molecules.

It is also possible that the reaction solution contains the reaction components. Alternatively, the reaction components can be supplied in the apparatus, the covering device and/or the base surface. This provisioning can take place in many different ways.

It is particularly preferred, in this connection, that the reaction components are made available in a matrix, preferably in a gel, particularly preferably an agarose gel, and wherein the reaction components are released when the reaction solution is added and/or heat is supplied.

Provisioning by means of a gel or a gel-like matrix that only dissolves when heated is particularly very advantageous. Thus, the reaction solution with the target molecules can be filled in first, without primer or detection probes being displaced. For this purpose, the use of low-melting agarose is particularly preferred. Because heating has to take place for PCR in any case, the reaction components are released by means of heating at the beginning of the amplification step. Furthermore, the polymerase as well as all the chemicals for detection and/or amplification can also be supplied in this matrix. In this case, the reaction solution does not need to contain any further reagents other than the target molecules, because all the necessary reagents are supplied as reaction components. However, it is also possible that only part of the reagents, for example the primers or probes, are supplied as reaction components, and the other reagents are contained in the reaction solution along with the target molecules, and are applied to the apparatus subsequently.

The cavities of the filled base surface are preferably compartmented or isolated from one another by means of applying a covering device to them. As a result, desired reactions are made possible and undesired reactions or inhibitions are prevented.

Furthermore, the cavities can consist of a multi-ply composite or of track-etched membranes. The base surface can be a multi-fiber array, the basic unit of which is optical fibers. The surface can be a three-dimensional microstructure that contains individual regions that can be separated from one another to form compartments, by means of suitable process management, for example small columns, at the tip of which the amplification takes place. The material is preferably compatible with PCR reactions and/or with other DNA/RNA amplification methods, so that no inhibition or contamination takes place. It is preferred that the material can be produced in a manner compatible with mass production.

It is preferred that the base surface is produced from semiconductive amorphous, crystalline, quasi-crystalline and/or fiber-type material. These materials have proven to be advantageous, because in this way stable base surfaces can be produced in cost-advantageous manner. Preferably, the cavities of a base surface can be implemented by means of etching methods, among other things, such as, for example, by means of dry etching/reactive methods (including DRIE, Bosch process, ICP), wet chemical methods (including bases, acids, HF), or physical methods (including drilling, sputtering, ionic etching or forming processes such as injection molding and "hot embossing," LIGA method, micro-precision milling). The base surface and/or the covering device can preferably contain any desired coatings, preferably with biomolecules (DNA, RNA, proteins), metals, metal oxides or plastics.

The covering device can be either a DNA microarray or a simple substrate. It is furthermore preferred that the covering device consists of semiconductive amorphous, crystalline, quasi-crystalline and/or fiber-type materials, particularly preferably of glass, polymer, PDMS, PP, COC or COP. Furthermore, the covering device can be a composite of two materials. The substrate can also be an adhesive film, preferably an adhesive film for microtiter plates that can be used for PCR. Furthermore, a substrate can be coated with a further material (e.g. with PDMS). In this connection, attention must be paid to ensure that the material is compatible with the PCR reactions and does not cause any inhibition or contamination.

It is known to a person skilled in the art that a DNA microarray comprises reagents, preferably DNA sequences, which are preferably present in the form of spots. It can be preferred that a DNA microarray is present on the covering device or in the cavities, wherein it can also be preferred that further components that are needed for PCR are also introduced onto the covering device or into the cavities in the form of spots or surfaces.

DNA microarrays particularly serve to detect the mRNA amount of specific genes or rRNA of specific organisms. There are essentially two different types of DNA microarrays, on the one hand those in which cDNA, oligonucleotides or fragments of PCR products that correspond to the mRNA are imprinted onto the carrier material ("spotted microarrays"), and those that are based on synthetically produced oligonucleotides ("oligonucleotide microarrays"). These serve as probes that are applied at defined positions of a grid, for example on glass media.

The reaction components can optionally be applied to the covering device, or can already be spotted directly onto the base surface, preferably in the cavities. By means of this previous storage of specific reaction components, a DNA array is therefore implemented either by means of the covering device or by means of the base surface itself.

It is preferred that probes, particularly preferably different probes, are supplied in the cavities of the base surface as reaction components. At the same time, one type of primers is supplied in the covering device. Multiplexing is made possible, in this case, by means of the different defined regions of the base surface.

The target molecules can be bound to a surface of the base surface and/or of the covering device. It is also possible that the target molecules are made available loosely, localized in the form of an array.

The base surface itself can have properties similar to a DNA microarray, in other words can possess the properties listed above. For a preferred method according to the invention, the base surface is closed off with a covering device, either with a microarray or with a substrate, which does not contain any active components for the reaction (e.g. a simple polymer chip in the format of a microarray).

If a microarray is used as the covering device, this can be produced using any of the usual methods. These are preferably methods from the companies Affymetrix, Agilent, LC Sciences, Combimatrix, Nimlgen, Febit, Biofluidix. It is furthermore preferred that the primers are synthesized (e.g. from Biomers, IBA, IDT) and then applied to the substrate of the microarray using different spotting methods (dot-matrix printer, pin printer, TopSpot® system).

It is furthermore preferred that the base surface additionally has a region for making the reaction solution available. In this connection, it is preferred that the reaction solution is applied to the region for making the reaction solution available and that the reaction solution is distributed among the cavities by means of placing the covering device onto the cavities. It was completely surprising that the filling of the cavities is achieved by means of the design of the base surface according to the invention, without energy or further work steps having to be expended for this purpose. Preferably, the reaction solution that contains the target molecules is applied into or onto a specific region of the base surface that is intended for accommodation of a reaction solution. Subsequently, the covering device can be set onto this region with one end and folded over or pushed on and placed onto the base surface, so that the covering device is disposed within the liquid barrier. Furthermore, the covering device can be pressed on vertically, or pressed on at a slant, at first, and then folded shut like a lid, or pulled or pushed horizontally over the base surface (slipping). In the event of folding, the reaction solution is displaced beyond the chip and can thereby fill all the cavities. In the event of pushing, the reaction solution is pushed ahead at the front edge and thereby fills the base surface until it is completely used up.

The base surface is structured in such a manner that a reaction solution can be filled in without or with only little dead volume. This is implemented, among other things, by means of the barriers at the edge of the base surface, and by the geometry of the cavities, which permits self-filling. The Concus-Finn conditions are preferably met.

It is furthermore preferred that the base surface additionally has a reservoir for accommodation of excess reaction solution. By means of this embodiment, clean work is made possible, and the general risk of contaminations in the work area is reduced.

It is preferred that the covering device covers the cavities after the base surface and the covering device have been arranged relative to one another, wherein it can also be advantageous that the covering device does not cover all the cavities, but rather only a selection of them. The reaction solution, which is preferably a hydrophilic liquid that comprises the target molecules to be analyzed, is preferably conveyed into the cavities autonomously. It is not necessary to introduce the reaction solution into the cavities using a filling apparatus (e.g. a pipette). This represents a significant advantage as compared with the prior art. This means that it becomes possible, by means of the invention, to supply reaction components in the cavities and/or on the covering device, so that only the target molecules and, if necessary, further reagents for the amplification reaction or the derivatization reaction have to be introduced. In this connection, the reaction components can possess different constituents and functions, and thereby different regions of a target sequence can be analyzed in a base surface by means of digital PCR, for example. Accordingly, different reactions can be carried out on a base surface, thereby making "multiplexing" possible and significantly reducing the work effort and the costs.

Furthermore, it is preferred that the target molecules and/or the product molecules are subsequently analyzed, sequenced and/or derivatized. In this connection, the apparatus is once again divided into the covering device and the base surface. The part of the apparatus on which the reaction components were supplied, preferably probes, is then available for further analysis methods.

In a further preferred embodiment, the invention relates to an apparatus for carrying out one of the methods named, characterized in that the apparatus comprises a base surface with cavities and a covering device, and wherein the covering device is preferably a microarray, wherein the base surface and the covering device can be arranged, relative to one another, in such a manner that reaction spaces are formed.

It is preferred that the covering device comprises capture molecules that are immobilized on the covering device.

In this connection, it is particularly preferred that the apparatus additionally comprises a cassette that can accommodate the base surface and the covering device and brings them into a state that is advantageous for the reaction. Furthermore, this apparatus can make a filling device available. The entire apparatus furthermore prevents contamination with reaction solution and reaction components. In the case of the amplification system PCR, the apparatus guarantees good introduction of heat. In the case of mechanical capping, this maintains close mechanical contact between the base surface and the covering device during the reaction.

It is particularly preferred that the special embodiments of the method as described were implemented in the apparatus. It is particularly preferred that the base surface of the apparatus has a liquid barrier that forms an edge around the cavities, wherein the liquid barrier is preferably a chemical and/or physical barrier.

An immense advantage of the invention lies in the reduction of the reaction volume, thereby lowering the general costs and minimizing the risk of contamination and the through-flow. The invention can therefore be used, for example, for the determination of mutations in non-invasive diagnosis, because here, high-resolution analysis of individual molecules and amplification of these individual molecules is required. It is preferred that one target molecule or preferably one DNA sequence, respectively, is present in a reaction volume or a cavity, respectively. In this way, it is prevented that special sequences are preferred in PCR, and the formation of undesired primer dimers is reduced. The invention can particularly preferably be used for detection of point-mutation-related illnesses. Thus, the combination of digital PCR and enrichment of fetal DNA under parenteral DNA, for example, allows simple detection of illnesses caused by point mutations. In the prior art it has not been described, for example, that the detection of aneuploidy is possible with systems for the enrichment of fetal DNA under parenteral DNA. By means of the combination of a technique for prior enrichment of fetal DNA and subsequent analysis of it in a multiplex PCR system according to the invention, the invention thereby provides a successful system, for the first time, which can be used for non-invasive detection of pediatric illnesses.

A further preferred area of application of the method according to the invention is the detection of Single Nucleotide Polymorphism (SNP) and gene aberrations. For this purpose, primers and probes are generated in such a manner that specifically only one sequence with the respective SNP is expanded. The detection can take place by means of a color code (in other words, for example, A=green, C=red, G=blue, T=dark red) or by means of spatial separation of four individual spots. In this connection, positive spots allow quantification. Preferably, only one spot responds (homozygous heredity of SNP, mother and father identical), or precisely two spots respond, which preferably yield approximately the same number of positive signals (heterozygous heredity, 50% father 50% mother). By means of this method, gene aberrations such as forms of trisomy (⅔ spot 1 and ⅓ spot 2 or 3 spots each with ⅓ signal), duplications or deletions can also be detected.

Furthermore, it is preferred that the method according to the invention is used for detection of specific nucleic acid sequences (genotyping). Here, the matching primers and a probe are supplied on the respective spot, such as, for example, resistance genes and internal "house-keeping genes." Positive signals allow quantification. The relative comparison between house-keeping genes and resistances allows a statement as to how many and which ones of the tested genomes demonstrate resistance.

It is furthermore preferred that the method is used for quantification of one or more DNA concentration(s). In this embodiment, a volume series is introduced into the base surface, so that the cavities are filled with different volumes. Furthermore, a general primer and probe system is introduced into the base surface. Only the sample is added. The surface can be homogeneously coated with the primer system, or can contain some stripes/spots at reference genes. Because of the decreasing volumes, precisely one or fewer DNA strands will be present per cavity at some point, on average, starting from a specific volume. Digital PCR takes place here now. A determination of the DNA concentration can then be made on the basis of the cavities that are no longer only positive.

It is also preferred that multiple different species/subtypes are "digitalized." This allows determining the total bacteria count and the number of harmful subtypes, e.g. EHEC, etc., from an *E. coli* population, for example, in a single batch. Here, digitality is not achieved in that fewer target molecules than cavities are present, but rather preferably in that target molecules of different subtypes are amplified and detected in the cavities.

It is furthermore an advantage of the invention that all known applications of digital PCR can be covered with the method.

In a further preferred embodiment, the invention relates to a kit comprising a base surface and a covering device, as well as a reaction solution (without a sample). Then, all that is necessary is to place the target molecules into the reaction solution that does not contain a sample, and to apply the finished reaction solution onto the base surface. The invention accordingly also relates to a kit for carrying out a dPCR. It was completely surprising that it was possible to produce a kit with which the method according to the invention could be carried out. In this connection, it could not be expected that the apparatus, together with the supplied reaction components, can be permanently stored, without the reaction components losing their function. The kit according to the invention can therefore be stored over an extended period of time, and thereby makes carrying out the method according to the invention many times easier.

Using the method according to the invention, up to $10^6$ targets can be detected. In this connection, the number depends on the size of the individual cavities and the size of the spots on the array.

It is an advantage of the invention that only standard equipment is required. For example, devices that are already commercially available, such as, for example, PCR cyclers for slide holders (Slide-Cycler) or as an insert for a microtiter plate can be used for PCR. For detection, a standard device can be used for reading out DNA microarrays (array scanner), for example.

By means of a simple redesign of the DNA probes (modification of the DNA sequences) on the array, the detection system can be tailored to different target molecules, so that the method can be universally used. Furthermore, the sensitivity can be defined by way of establishing the number of cavities per spot.

The cavities of the base surface can have different sizes within a base surface, and for this reason, a reaction solution can be investigated without prior quantification. By means of a skillful selection of the reactor volumes, it will always be possible to find a region that is "digital." And the other regions can provide additional information by means of the MPN method. A large concentration range of a sample solution can be covered by means of multiplication of the chamber sizes. In this way, meaningful results can be achieved without prior quantification of the DNA in the sample. As a result, time and handling steps are saved.

The signals are preferably read out digitally, so that only the end result of the analysis needs to be evaluated, and the reaction device and the detection device can be coupled for this purpose. In this way, apparatus expenditure can be minimized.

The base surface can be produced, for example, by means of injection-molding or hot embossing, whereas production systems that have been established for decades can be used for the covering device. Therefore the base surface can be made available by means of advantageous production methods.

In contrast to some methods of the prior art, which use oil for the generation of reaction compartments, in this method division of a sample into many cavities takes place mechanically (without oil), preferably using the covering device. In this way, all the disadvantages described in the prior art are circumvented.

It is advantageous that the product molecule, preferably the amplificate, can be bound in the base surface and/or on the covering device surface, and thereby also allows a later detailed analysis such as sequencing, for example, or recovery of the corresponding gene material (e.g. recovery of the generated PCR product, possibility of sequencing a DNA microarray after the reaction), if necessary or desired.

The teaching according to the application is particularly characterized by the following characteristics:

- existence of an urgent need, which has remained unresolved for a long time, for the problem solution accomplished with the invention;
- the simplicity of the solution speaks for inventive activity, particularly since it replaces complicated teachings;
- improvement, increase in performance, reduction in costs, savings of time, material, work steps, and costs;
- increased reliability, elimination of errors, quality improvement, freedom from maintenance, greater effectiveness, higher yield.

In particular, the advantageous embodiments of the invention demonstrate at least one or more of the said advantages.

EXAMPLES

Figure 2:
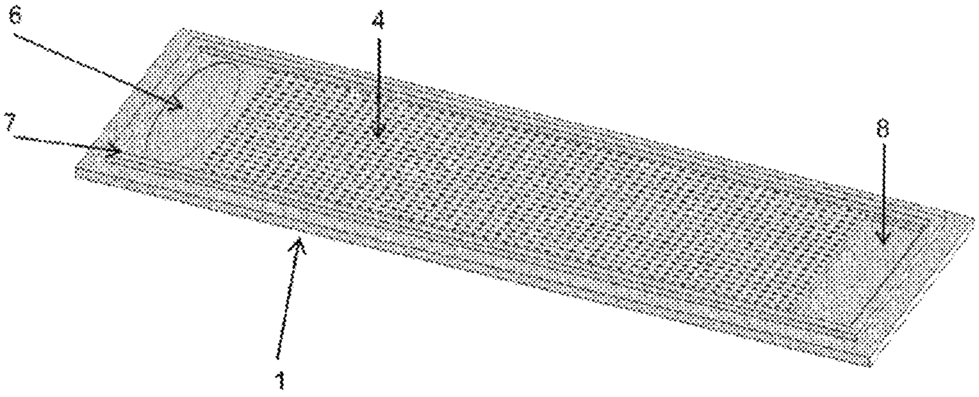
Figure 2:
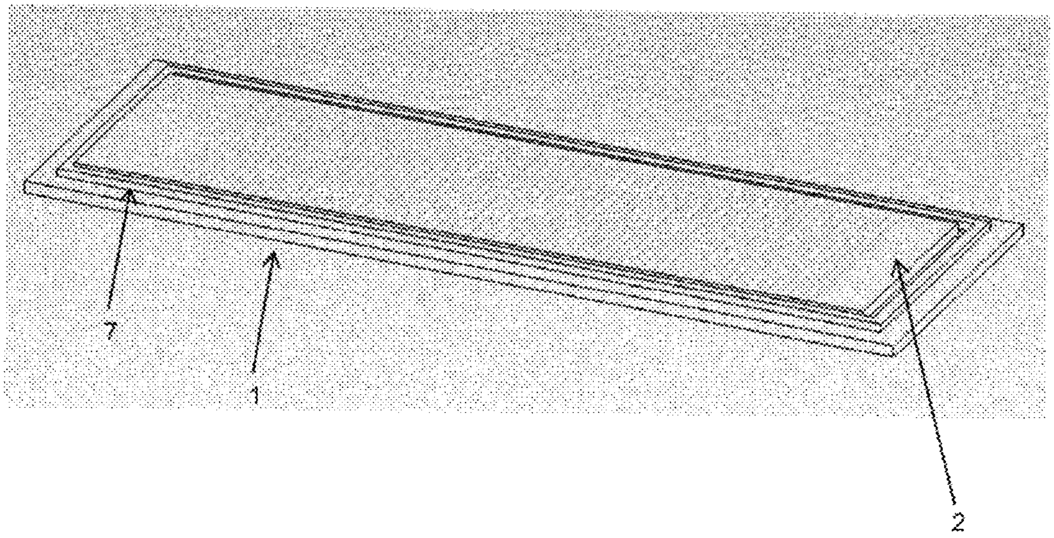
Figure 3:
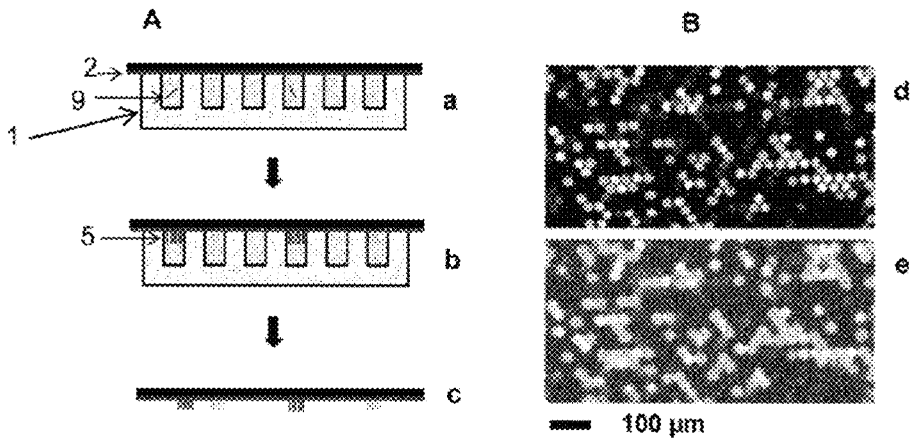
Figure 4:
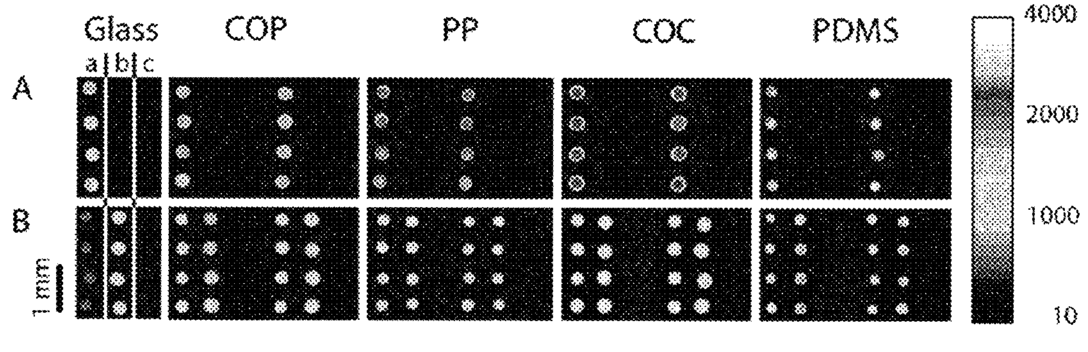

In the following, the invention will be explained using figures and an example, without, however, being restricted to these. The figures show:

FIGS. 1.1 and 1.2 exemplary embodiment of a preferred method and of the corresponding apparatus, FIG. 2A, 2B preferred design of an apparatus, FIG. 3 preferred method using dCPR, FIG. 4 immobilization of PCR primers and subsequent solid-phase PCR on a model system.

For solid-phase PCR, it is a prerequisite that corresponding surfaces be coated with PCR primers, so that the PCR primer is accessible/available for extension by means of a DNA polymerase. Both the surface of the base surface and the surface of the covering device were coated with PCR primers (FIG. 3*a*). The covering device is preferably a PDMS slide. A DNA target sequence was mixed with a PCR reaction mixture and introduced into the base surface. The base surface was covered with the covering device, in this case a DNA microarray (FIG. 2). In order to carry out digital PCR, the DNA target sequence is diluted, so that each individual cavity contains either one or no DNA molecule. By means of the subsequent PCR reaction, a PCR amplification product is generated in each cavity that previously contained one DNA molecule, and this product is particularly bound to the surface of the base surface (FIG. 1). Because, in the present example, the covering device was also provided with solid-phase primers, the DNA amplificates were also immobilized on the covering device. In this way, an exact copy of the distribution of the product molecules of the base surface is made available on the microarray (covering device) (FIG. 1D). In order to visualize the amplificates, hybridization is carried out on PTP (pico-titer plates) and on the covering device.

It was possible to detect immobilization of PCR primers suitable for solid-phase PCR, with full functionality, on base surfaces composed of GS FLX titanium chips, GS FLX chips, and furthermore on typical materials that are used in microfluidics. These include glass, polydimethylsiloxane (PDMS), cyclo-olefin polymer (COP), cyclo-olefin copolymers (COC), and polypropylene (PP).

For carrying out the method in the case of digitality, <<1x10^5 target molecules were placed into 1x10^5 cavities on a base surface with a size of 13x13 $mm^2$. A GS FLX titanium chip was used as the base surface. After 50 thermocycles, the signals on the base surface and on the covering device were automatically counted. A PDMS slide was used as the covering device. When digital solid-phase PCR was carried out using two different DNA sequences, a two-color image was generated after hybridization (FIG. 3, *b*). In this connection, good comparability of base surface and covering device was always achieved.

This experiment is an example of parallel analysis of the concentrations of two different DNA target molecules. The respective concentration can be calculated for the colors red and green. Yellow counts as red and green at the same time. The total DNA concentration for each target molecule is the number of positive cavities divided by the number of all the cavities divided by the volume of a cavity.

FIG. 1.1 shows a preferred embodiment of the invention. In (A), a covering device 2 is shown, which is a DNA microarray. Below that, a base surface 1 with cavities 4 is shown, where the cavities 4 are filled with a PCR reaction mix containing diluted DNA target molecules. (B) shows an enlargement of the spots 3 of the microarray 2 or of the cavities 4, respectively. In (C), it is shown how the apparatus is assembled. In this connection, covering device 2 and base surface 1 are arranged relative to one another in such a manner that the cavities 4 and the spots 3 of the microarray 2 come into contact with one another. In the case shown, the spots 3 of the microarray 2 cover multiple cavities 4 of the base surface 1, in each instance. The amplification reaction also takes place in this step. A temperature cycle protocol is used, and DNA amplificates 5 are produced. In this connection, amplificates 5 occur only in the cavities 4 into which a target molecule was introduced. In the exemplary embodiment shown, the PCR products 5 (=product molecules in the sense of the invention) are covalently immobilized on capture molecules of the microarray 2. Here, the preferred mechanism is solid-phase PCR. Subsequently, the covering device 2 and the base surface 1 are separated from one another again. The covering device 2 is washed and preferably stained with a two-color hybridization and scanned. In (D), the result of the method is shown. A PCR product 5 of two different DNA sequences (1500 and 350 base pairs long) is detected on the microarray 2.

FIG. 1.2 shows a further preferred embodiment of the invention. In (A), a covering device 2 is shown, which is a simple substrate. Underneath that, a base surface 1 with cavities 4 is shown, where the cavities 4 are filled with a PCR reaction mix containing diluted DNA target molecules. Furthermore, a microarray was spotted onto the base surface 1, so that the reaction components were supplied in the base surface 1. In this connection, the spots 3 are larger than the cavities 4, so that there are always multiple cavities 4 in a spot 3. (B) shows an enlargement of the spots 3 of the base surface 1 and of the cavities 4. In (C), it is shown how the apparatus is assembled. In this connection, covering device 2 and base surface 1 are arranged relative to one another so that the cavities 4 were closed off by the covering device 2. The amplification reaction also takes place in this step. A temperature cycle protocol is used, and DNA amplificates 5 are produced. In this connection, amplificates 5 occur only in the cavities 4 into which a target molecule was introduced. In the exemplary embodiment shown, the PCR products 5 (=product molecules in the sense of the invention) are covalently immobilized on capture molecules of the base surface 1. Here, the preferred mechanism is solid-phase PCR. Subsequently, the covering device 2 and the base surface 1 are separated from one another again. The base surface 1 is washed and preferably stained with a two-color hybridization and scanned. In (D), the result of the method is shown. A PCR product 5 of two different DNA sequences (1500 and 350 base pairs long) is detected on the base surface 1.

FIG. 2 shows the possible design of a base surface 1 in the sense of the invention. The base surface 1 shown has a region 6 into which the reaction solution to be investigated is introduced. After the cavities 4 are filled and closed off with a covering device 2, the covering device 2 is enclosed by a raised barrier 7. The apparatus furthermore has a reservoir 8 that holds excess sample volume.

FIG. 3: In (a), a base surface 1 is shown, which is filled with a PCR reaction mix containing diluted DNA target molecules 9 and was closed off using a covering device 2. While an amplification reaction is carried out, a PCR product 5 is produced in the cavities 4 that contain target molecules 9. The PCR product 5 binds covalently to immobilized DNA capture molecules, in this case solid-phase primers, both on the base surface 1 and on the covering device 2. The covering device 2 and the base surface 1 are separated from one another again and both surfaces are washed and preferably stained with a two-color hybridization and scanned.

FIG. 3 (B) shows the results of the digital PCR. A PCR product 5 of two different DNA sequences (1500 and 350 base pairs long) is detected on the covering device 2 (*d*) and on the base surface 1 (*e*). The three colors red (dark), green (medium) and yellow (light) show the positive cavities 4 and the "mirror image" of the positive cavities 4 on the covering device 2, respectively.

FIG. 4 shows Cy5 scans of DNA microarrays containing a Cy5-labeled primer as a non-extendable spotting control (column a), an extendable primer as an extension control (column b), and a non-labeled and non-extendable primer as a negative control (column c). Four rows of spots were used per reaction solution. The arrays were scanned before (Series A) and after (Series B) solid-phase PCR and staining. It was possible to observe highly specific extensions of the extendable primers in all polymers and also on glass.

The two results together (FIGS. 3 and 4) show that for one thing, it is possible to carry out digital PCR in which the PCR product is immobilized on a solid phase (FIG. 3, B, *d* and *e*). Furthermore, it was shown that solid-phase PCR can be carried out with primers immobilized in the format of a traditional DNA microarray (FIG. 4). The combination of these two results creates a preferred embodiment of the new method for multiplexed digital PCR. This is neither known nor made obvious in the prior art.

REFERENCE SYMBOL LIST

1 base surface
2 covering device
3 defined regions on the covering device (spots)
4 cavities
5 product molecules
6 region for application of a sample
7 barrier
8 reservoir that holds possible excess sample volume
9 DNA target molecule

The invention claimed is:

1. Method for detection of at least one target molecule and/or product molecule, comprising:
- a) providing:
  - (i) a base surface comprising 1-$10^{10}$ cavity/cavities and a liquid barrier that forms an edge around the cavity/cavities, and
  - (ii) a substrate or a microarray adapted to cover the base surface,
  - (iii) reaction components in defined regions of the cavity/cavities of the base surface and/or in defined regions on the substrate or microarray, wherein there are at least two defined regions each comprising a first and second reaction component which differ from each other, and wherein each reaction component comprises at least one primer and/or probe, which is attached to the substrate or microarray, and
- b) adding a reaction solution comprising the at least one target molecule,
- c) covering the base surface, within the liquid barrier, with the substrate or microarray, wherein the reaction solution penetrates into the cavity/cavities and each cavity of the base surface forms a reaction space as result of said covering,
- d) wherein, within the reaction spaces, the reaction solution comes into contact with the reaction components and an amplification reaction, a detection reaction and/or a derivatization reaction ensues forming product molecules, and
- e) detecting at least one target molecule and/or product molecule, wherein at least two different sections of the target molecule and/or product molecule are detected in separate reaction spaces and/or at least two different target molecules and/or product molecules are detected in separate reaction spaces.

2. The method of claim 1,
wherein the defined regions are spots of the microarray.

3. The method of claim 1,
wherein the defined regions lie in the cavity/cavities of the base surface.

4. The method of claim 2,
wherein one spot of the microarray covers multiple cavity/cavities of the base surface.

5. The method of claim 1,
wherein the reaction components are immobilized on the microarray.

6. The method of claim 1,
wherein the reaction components are made available in a matrix, and wherein the reaction components are released when the reaction solution is added and/or heat is supplied.

7. The method of claim 1,
wherein the amplification reaction is digital PCR and/or digital solid-phase PCR.

8. The method of claim 1,
wherein the reaction solution comprises nucleic acids, proteins, natural substances, intercalating pigments, enzymes, additives, viruses, prokaryotes, eukaryotes, fragments of synthetic molecules and/or biomolecules.

9. The method of claim 1,
wherein the base surface has 2 to $10^{10}$ cavities and the cavities possess a volume of 1 fL to 1 mL.

10. The method of claim 1,
wherein the liquid barrier is a chemical and/or physical barrier.

11. The method of claim 1,
wherein the base surface further comprises an additional region comprising an indentation within the base surface (i) adjacent to the cavity/cavities and (ii) within the liquid barrier that forms an edge around the cavity/cavities which is adapted to hold the reaction solution and is connected to the cavity/cavities.

12. The method of claim 1,
wherein the base surface further comprises a reservoir comprising an indentation within the base surface (i) adjacent to the cavity/cavities and (ii) within the liquid barrier that forms an edge around the cavity/cavities, which is connected to the cavity/cavities and which is adapted to accommodate excess reaction solution from the cavity/cavities.

13. The method of claim 1,
wherein the base surface is made of semiconductive amorphous, crystalline, quasi-crystalline, fiber-type materials or combinations thereof.

14. The method of claim 1,
wherein the substrate or microarray is made of semiconductive amorphous, crystalline, quasi-crystalline, fiber-type materials or combination thereof.

15. The method of claim 11,
wherein the reaction solution is placed onto the additional region, and the reaction solution is distributed among the cavity/cavities by placing the substrate or microarray onto the apparatus.

16. The method of claim 1,
wherein the product molecules are subsequently analyzed, sequenced and/or derivatized.

17. The method of claim 6, wherein the matrix is a gel.

18. The method of claim 17, wherein the gel is agarose gel.

19. The method of claim 9, wherein the base surface has $10^2$ to $10^8$ cavity/cavities.

20. The method of claim 14, wherein the crystalline or fiber-type materials are glass, polymer and combination thereof.

21. The method of claim 1, wherein the substrate has a plane surface.

22. Method for detection of at least one target molecule and/or product molecule, comprising:

a) providing:
  (i) a base surface comprising $1\text{-}10^{10}$ cavity/cavities and a liquid barrier that forms an edge around the cavity/cavities, and
  (ii) a substrate or a microarray adapted to cover the base surface,
  (iii) primers and/or probes in regions within the cavity/cavities of the base surface and/or in spots on the microarray, wherein there are at least two regions within the cavity/cavities or within the at least two spots each comprising a first and second primer and/or probe which differ from each other, b) adding a reaction solution comprising the at least one target molecule, c) covering the base surface, within the liquid barrier, with the substrate or microarray, wherein each cavity of the base surface forms a reaction space as result of said covering, d) wherein, within the reaction spaces, the reaction solution comes into contact with the primers and/or probes and an amplification reaction, a detection reaction and/or a derivatization reaction ensues forming product molecules, and e) detecting at least one target molecule and/or product molecule, wherein at least two different sections of the target molecule and/or product molecule are detected in separate reaction spaces and/or at least two different target molecules and/or product molecules are detected in separate reaction spaces.

23. The method of claim 22, wherein the primers are provided in regions within the cavity/cavities of the base surface and the base surface is covered by the substrate, wherein the substrate has a plane surface facing the cavity/cavities, the target molecules are nucleic acids, and the amplification reaction is a PCR.

* * * * *